United States Patent [19]
DeVito

[11] Patent Number: 5,249,124
[45] Date of Patent: Sep. 28, 1993

[54] MULTI-ISOTOPE IMAGING USING ENERGY-WEIGHTED ACQUISITION FOR, E.G., MYOCARDIAL PERFUSION STUDIES

[75] Inventor: Raymond P. DeVito, Palatine, Ill.

[73] Assignee: Siemens Gammasonics, Inc., Hoffman Estates, Ill.

[21] Appl. No.: 685,940

[22] Filed: Apr. 16, 1991

[51] Int. Cl.⁵ .................. G06F 15/00; G01T 1/166; A61B 6/00
[52] U.S. Cl. .................. 364/413.24; 364/413.16; 250/363.04; 378/14
[58] Field of Search .............. 364/413.24, 414, 581, 364/724.12, 485, 413.16; 250/363.02, 363.04, 363.07, 367, 369; 378/901, 14, 15

[56] References Cited

U.S. PATENT DOCUMENTS 4,575,810 3/1986 Stoub .................. 364/581
4,873,632 10/1989 Logan et al. .......... 364/413.13

Primary Examiner—Roy N. Envall, Jr.
Assistant Examiner—Khai Tran
Attorney, Agent, or Firm—Mark H. Jay

[57] ABSTRACT

A multi-isotope study is carried out using a plurality of imaging agents which are imaged simultaneously. The information obtained is weighted using as many energy weighting functions as there are isotopes. The weighting reduces "crosstalk" between each of the single-isotope images which are produced as a result of the study. This produces improved results in, for example, dual-isotope (Tc-99m and Tl-201) myocardial perfusion studies.

7 Claims, 5 Drawing Sheets

MULTI-ISOTOPE IMAGING USING ENERGY-WEIGHTED ACQUISITION FOR, E.G., MYOCARDIAL PERFUSION STUDIES

BACKGROUND OF THE INVENTION

The invention relates to nuclear medicine, and more particularly relates to nuclear medicine studies in which more than one isotope is administered to the patient. In its most immediate sense, the invention relates to dual-isotope myocardial perfusion studies.

It has long been known to administer e.g. two radioisotopes to a patient and to form two images of the patient, one relating to one isotope and the other relating to the other isotope. U.S. Pat. No. 3,904,530 teaches apparatus which is designed to be used in such a study. Presently, the only significant clinical application of a dual-isotope study is a parathyroid study. Such a study is designed to detect the existence of an adenoma (which takes up Tl) on the thyroid (which takes up both Tc and Tl). In this study, subtraction of the Tc image from the Tl image will reveal the adenoma.

Recently, Daniel S. Berman, M.D. at the Cedars-Sinai Medical Center (Los Angeles, Calif.) has proposed to improve existing myocardial perfusion studies by using a dual-isotope technique and utilizing a recently developed Tc-99m sestamibi pharmaceutical marketed by Du Pont Merck Pharmaceutical Co. (Wilmington, Del.) under the CARDIOLITE trademark. The present invention has particular utility in such studies and to understand this utility it is necessary to understand the purposes and protocols used in myocardial perfusion studies. This will now be explained.

There are two major categories of cardiac problems. One category includes patients who have cardiac infarctions (dead myocardial tissue). The other category includes patients who have arteriosclerosis (disease of the coronary arteries). Clinically, it is necessary to distinguish between these two categories because they are managed differently. (When a cardiac patient is shown to have an infarcted myocardium, no surgical intervention is used and the patient is medicated and instructed to avoid heavy physical activity. When a cardiac patient is shown to have arteriosclerosis, surgical intervention can be used to correct the problem.)

A myocardial perfusion nuclear medicine study is presently used to distinguish between these two categories of problems. In such a study, Tl (this is most commonly used, but Tc can also be used) is administered to a patient while the patient has reached the point of maximum effort in a stress test. (The stress test can be administered physically, in which case the patient is placed on a treadmill. Alternatively, for bedridden patients, the stress test can be administered pharmacologically by administering a dipyridamole drug sold under the I.V. PERSANTINE trademark by Du Pont Merck Pharmaceutical Co. This also increases blood flow to the heart muscle.) The Tl collects in the myocardium (heart muscle) and its initial distribution within the myocardium shows the regions where the myocardium is perfused with blood flow. Then, the patient's heart is imaged in a gamma camera to record this heart-under-stress blood perfusion. Afterward, the patient is permitted to rest so that the stress conditions entirely dissipate. As this happens, the Tl redistributes itself within the heart, and after a period of time (aided in some, but not all, instances by another injection of Tl) the distribution of Tl within the myocardium represents blood perfusion in the heart at rest. Then, the patient's heart is imaged a second time in a gamma camera to record this heart-at-rest blood perfusion.

If a region of the myocardium shows Tl uptake when the heart is at rest, this indicates that this region contains living tissue. If the same region of the myocardium then lacks Tl uptake when the heart is stressed, this indicates the presence of arteriosclerosis which prevents blood from reaching region under stress conditions. On the other hand, if a region of the myocardium shows no Tl uptake either at rest or under stress, this indicates that the region contains an infarction which blood does not perfuse.

This conventional myocardial perfusion protocol takes a long time. Typically, the study lasts an entire day. This is because each session in the camera lasts about an hour and the interval between sessions is four hours. Camera throughput is low and study cost is consequently high.

Dr. Berman's research has developed a study protocol which would drastically shorten the duration of such myocardial perfusion studies. According to this new study protocol, the resting patient is first injected with a Tl agent. In a few minutes, the Tl will be taken up by the heart in accordance with heart-at-rest blood perfusion. Thereafter, the patient is subjected to a stress test and injected, at peak stress, with the Tc CARDIOLITE agent. This agent too is taken up within a few minutes. Then, the patient is placed in a gamma camera and a dual-isotope study of the patient is conducted. Such a dual isotope study produces two images—a Tl image and a Tc image—of the patient's heart and the relationship between the images shows where heart muscle is affected by arteriosclerosis and where it is infarcted.

This new study protocol produces dramatic improvement in camera throughput, because the prolonged wait between injections is eliminated and only one camera session is needed instead of two. This is a major development because myocardial perfusion studies are the second most common application for nuclear medicine.

Conventional gamma cameras with dual-isotope capability are not able to make optimum use of this new study protocol. This is because there is a degree of crosstalk between the two acquisition channels, i.e. events from the Tc channel will be counted in the Tl channel and vice versa. In the case of parathyroid studies, this is not particularly disadvantageous, but in cardiac applications this would significantly degrade the diagnostic utility of the images produced. It would therefore be advantageous to provide gamma cameras with improved crosstalk characteristics so as to better benefit from this new study protocol.

One object of this invention is to provide method and apparatus which could be used in multi-isotope studies, particularly dual-isotope studies, wherein crosstalk between the resulting images would be reduced.

Another object is to provide method and apparatus which could be used to improve the images produced by a dual-isotope myocardial perfusion study.

A further object is to provide method and apparatus by which existing gamma cameras with dual-isotope capability could be retrofitted so as to be usable in dual-isotope myocardial perfusion studies.

Still another object is to improve on method and apparatus of this general type.

SUMMARY OF THE INVENTION

The present invention compensates for crosstalk between isotope by using as many energy weighting functions as there are isotopes in the study and applying these weighting functions to information acquired. Where the information is acquired on an event-by-event basis, each event is separately weighted using each function. Where the information is acquired on a frame-by-frame basis, each frame is weighted. Where the information is acquired on a spectral basis, the spectra are deconvolved.

By weighting all the information acquired, each event, frame, spectrum etc. is utilized in a statistically appropriate manner. This reduces crosstalk, which results from statistically inappropriate treatment of information.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
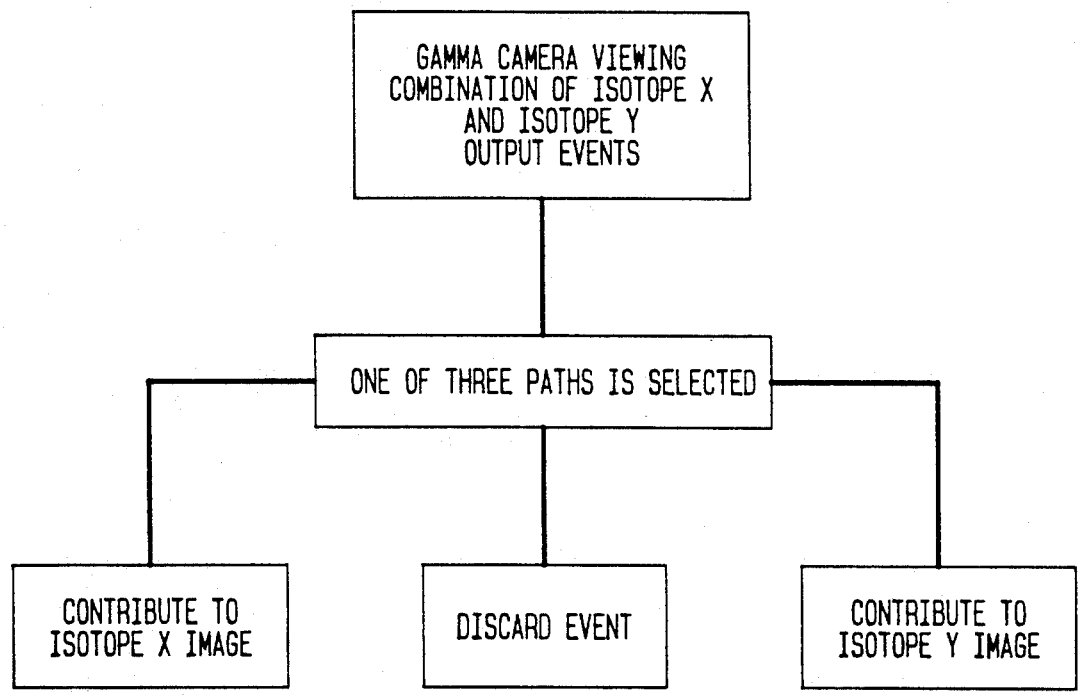
FIG. 1 shows how information is acquired and used in a conventional dual-isotope study.

In a conventional dual-isotope study, incoming scintillation events are tested for energies which lie in two pre-established energy windows. Thus, as shown in FIG. 1, the energy of each event is evaluated. If the energy of the event falls outside both windows, the event is completely discarded. If the energy of the event falls within, e.g., the Tl window, the event is counted as a Tl event and added to the set of events which will contribute to the formation of a Tl image. If the energy of the event falls within, e.g., the Tc window, the event is counted as a Tc event and added to the set of events which will contribute to the formation of a Tc image.

However, as is known to persons skilled in the art, the energy response of a gamma camera to monoenergetic gamma rays is not monoenergetic. As a result of many factors, events may be categorized in the wrong window and wrongly counted. If, for example, a dual isotope study is carried out with Tl-201 and Tc-99m, many of the Tc99m events will have energies that fall outside the Tc-99m window and inside the Tl-201 window. Likewise, Tl-201 events are not always counted as such and some of such events are counted as Tc-99m events. Such "crosstalk" causes the Tc image to be based on non-Tc events and causes the Tl image to be based on non-Tl events.

While this is not a major problem in the case of parathyroid studies, it is such a problem in the case of dual-isotope myocardial perfusion studies. This is because in such a perfusion study, the two isotopes are much more intermingled and the regions of interest are relatively small. For such a study to have sufficient clinical utility, the referenced "crosstalk" must be removed.

Figure 2:
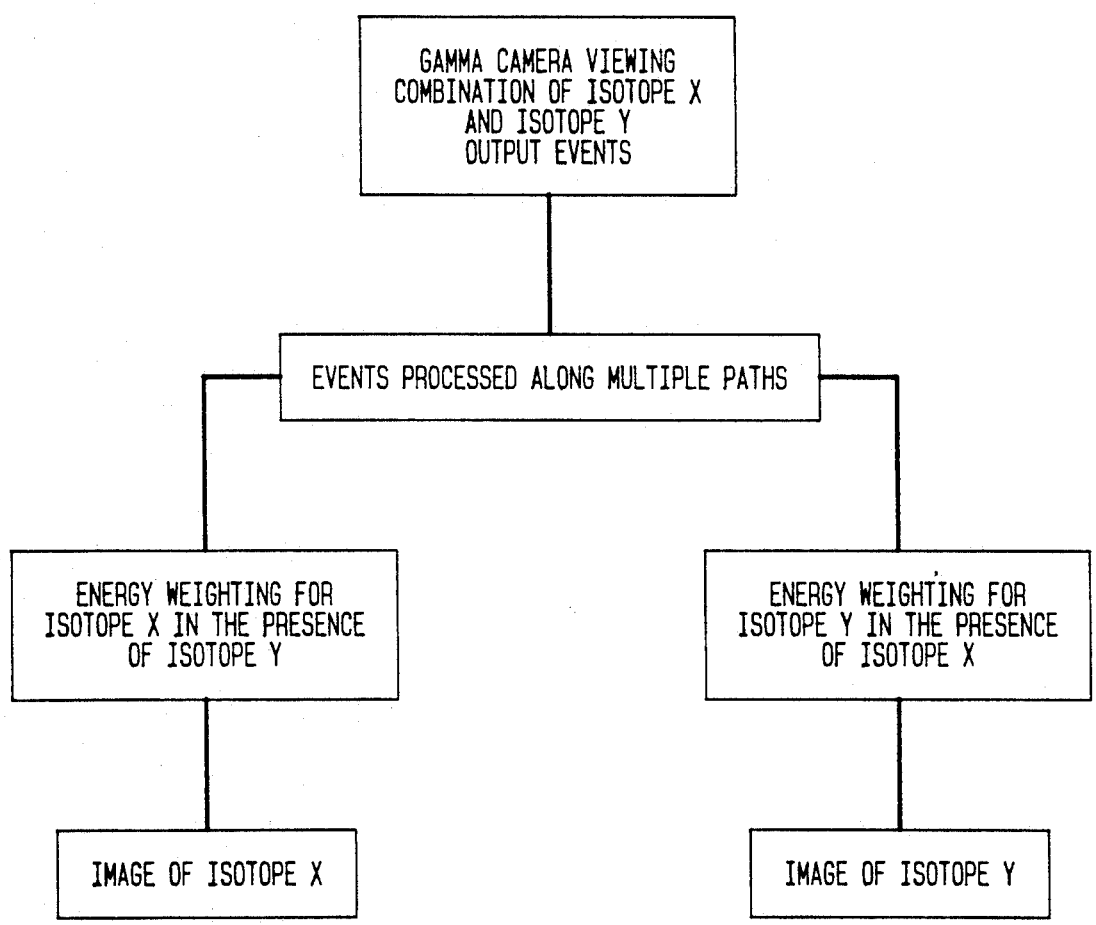
FIG. 2 shows how information is acquired and used in accordance with a first preferred embodiment of the invention.

In the first preferred embodiment as shown in FIG. 2, this is done in real time on an event-by-event basis. Where the study is of the dual-isotope type, each event contributes to each image, but the weight of the contribution is determined by weighting functions. Thus, where X and Y are the isotopes used, a first weighting function is for isotope X in the presence of isotope Y and a second weighting function is for isotope Y in the presence of isotope X. (The construction of these weighting functions will be discussed below. However, it is appropriate to note that in, e.g. a three-isotope study, there would be isotopes X, Y and Z, the first weighting function would be for isotope X in the presence of isotopes Y and Z, the second weighting function would be for isotope Y in the presence of isotopes X and Z, and the third weighting function would be for Z in the presence of X and Y.)

Figure 3:
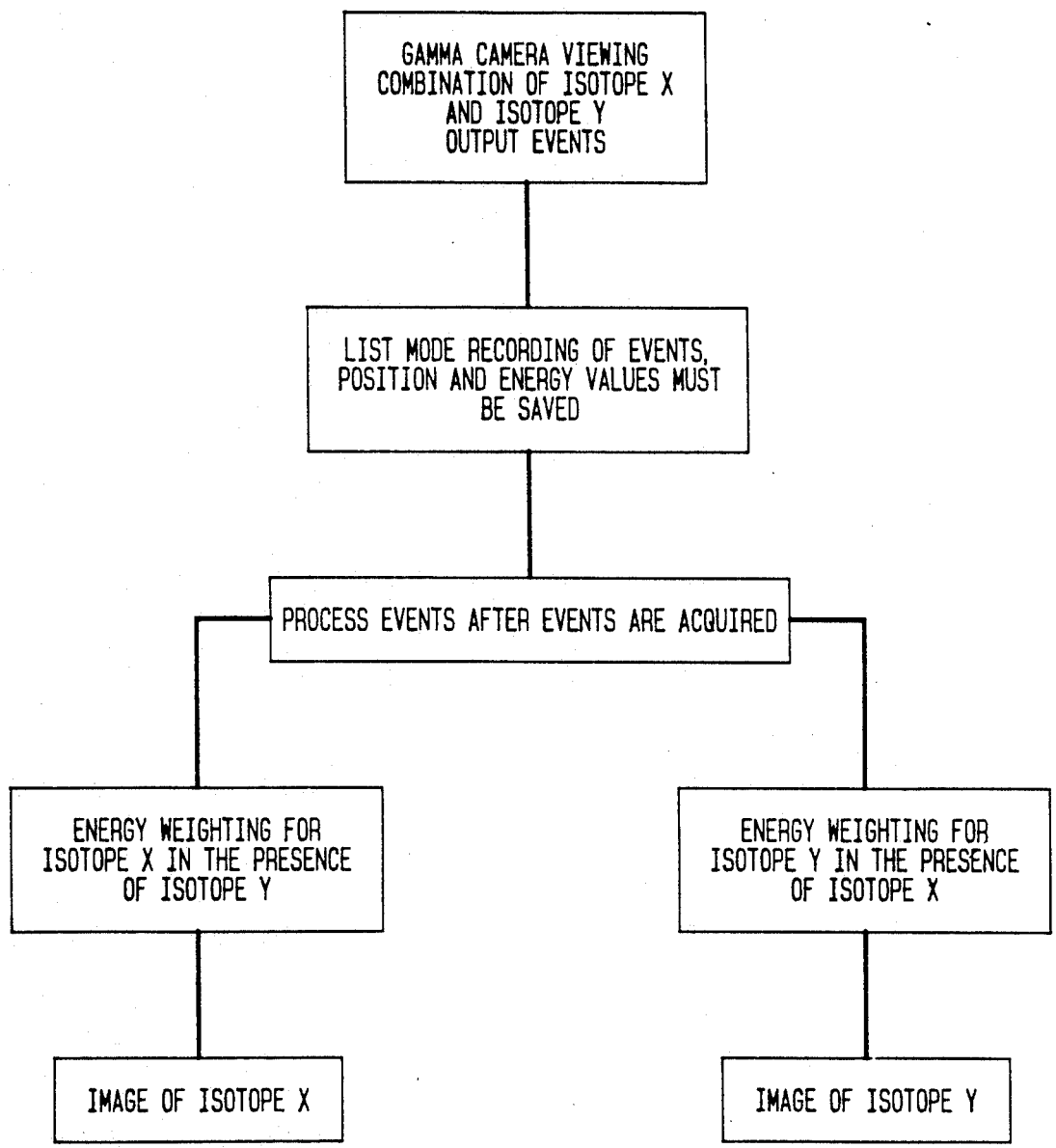
FIG. 3 shows how information is acquired and used in accordance with a second peferred embodiment of the invention.

In the second preferred embodiment as shown in FIG. 3, the same thing is done but on a post-processing basis. Here, each event is recorded and after the study has been completed, all the events are processed.

Figure 4:
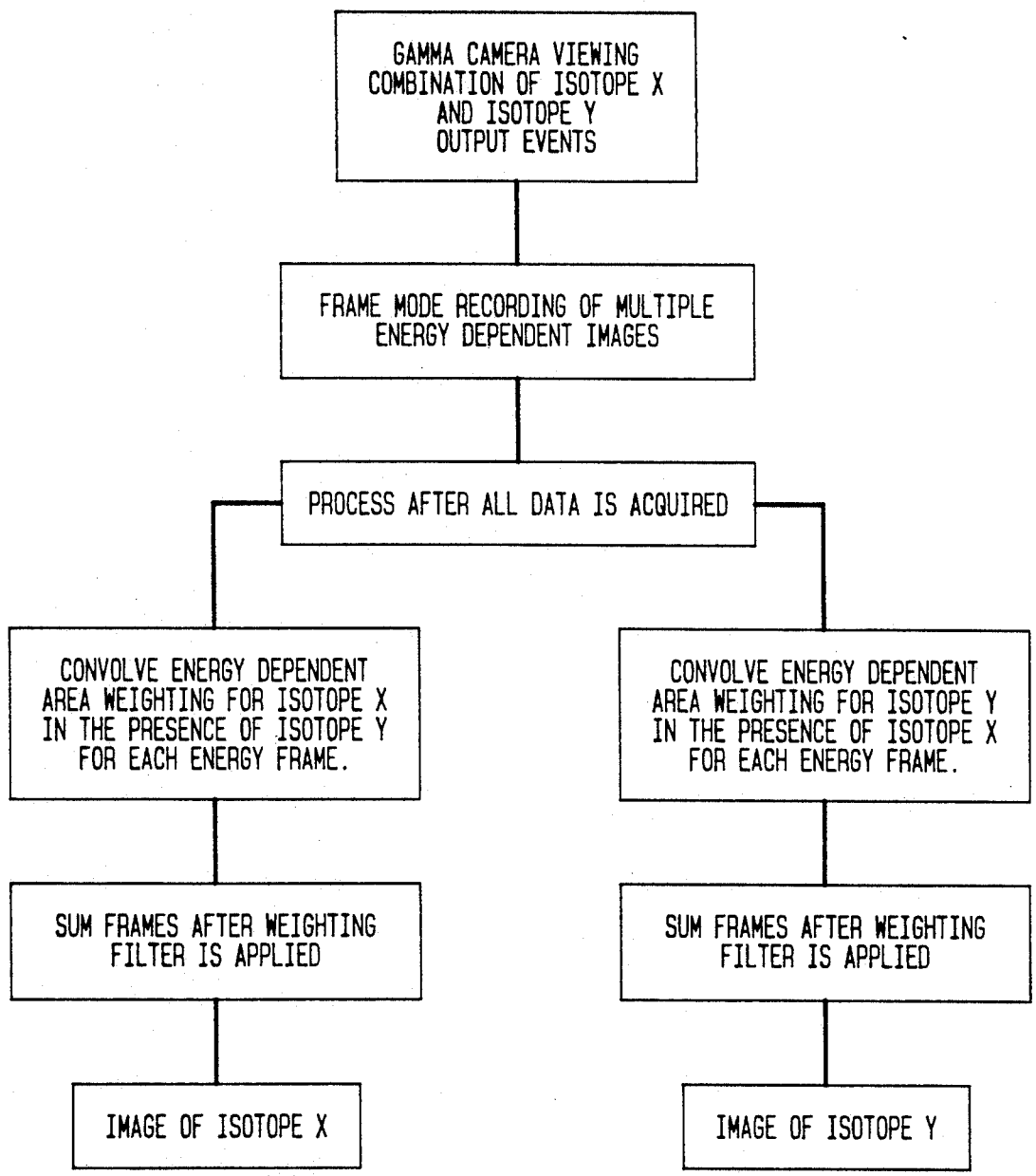
FIG. 4 shows how information is acquired and used in accordance with a third embodiment of the invention.

In the third preferred embodiment as shown in FIG. 4, post-processing is carried out, but this time on an energy-dependent frame-by-frame basis. Here, each frame is constructed from data which meets energy-based criteria and each frame, after appropriate weighting, contributes to each image. In this embodiment, the weighting is actually a convolution of the respective frame data.

Figure 5:
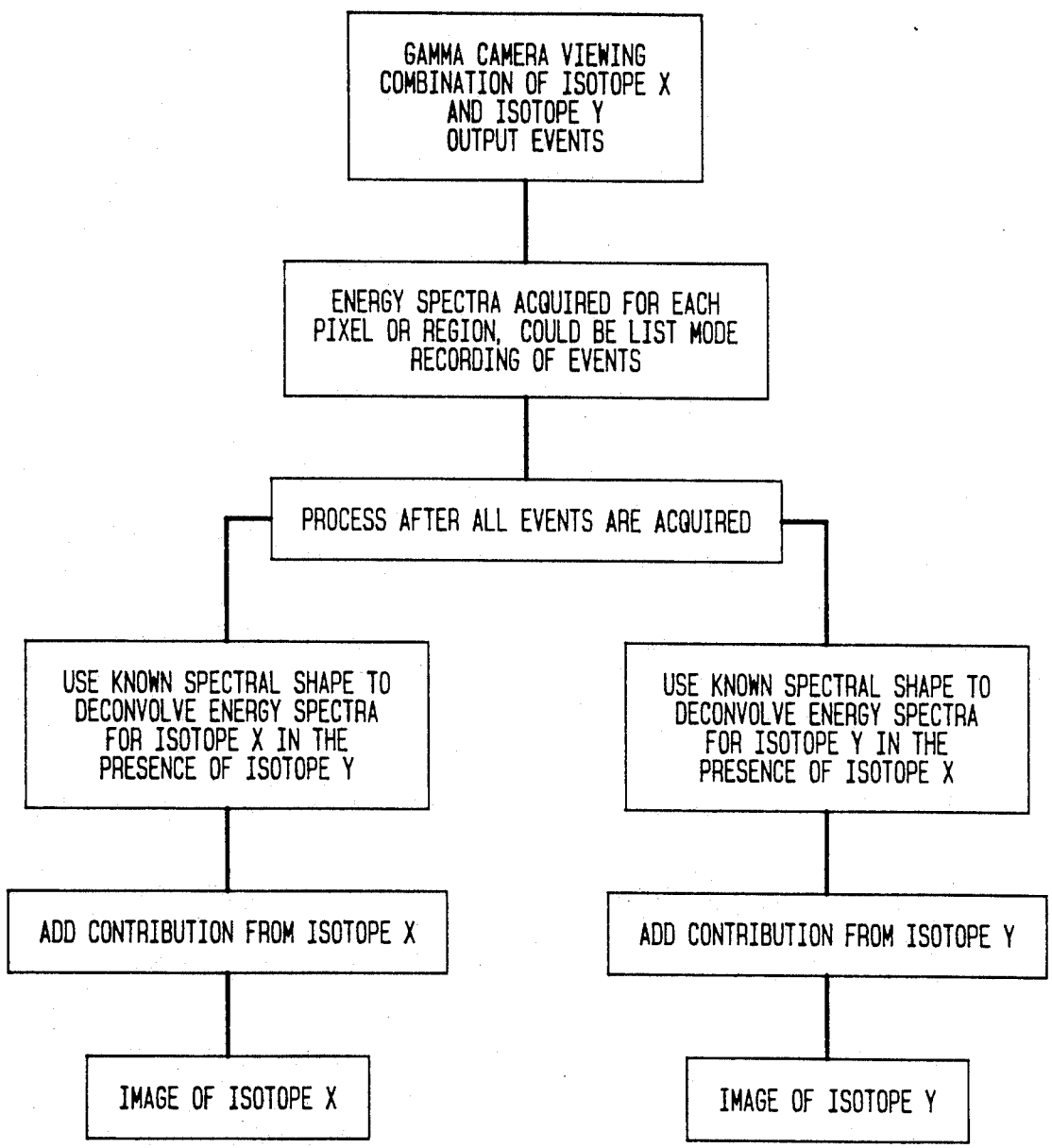
FIG. 5 how information is acquired and used in accordance with a preferred embodiment of the invention.

In the fourth preferred embodiment as shown in FIG. 5, which likewise is carried out in a post-processing mode, data is processed not on an event-by-event or a frame-by-frame basis, but rather on a region-by-region basis (it being understood that a "region" may be as small as a single pixel). For each region, the energy spectrum of events which occur in the region is accumulated and this spectrum is analyzed to deduce the amounts of the isotopes which are present. This analysis can be carried out by fitting the acquired energy spectrum with the known energy responses of, e.g., the two isotopes (X and Y) used. In other words, the energy responses for isotopes X and Y are known. For each region, the system determines what combination of isotopes X and Y would produce the acquired energy spectrum for each region in the image. This calculation will produce a quantity of isotope X and a quantity of isotope Y at that region. When the calculation is repeated for all regions of the image, the result is two separated images, one for isotope X and the other for isotope Y.

The image produced in accordance with each of the preferred embodiments can be either planar or tomographic. Obviously, production of a tomographic image requires the use of a rotating element so as to acquire the requisite number of views.

In the present instance, a weighting function was derived for use with Tc-99m and Tl-201 and was constructed to take account of resolution, noise and energy response uniformity of the camera system.

First, the Energy Dependent Point Source Response function (EPSF) is measured for each isotope. This procedure is described at page 344 of an article entitled *Determination of Weighting Functions for Energy-Weighted Acquisition* which was published in Feb., 1991 in The Journal of Nuclear Medicine, Vol. 32, No. 2, pp. 343-349.

Selection of an appropriate weighting function is then carried out by defining a generalized chi-square measure of quality (Q, see page 345 of the referenced article) for each of the isotopes and optimizing it using a gradient search method as is described at page 346. As is stated there, the optimization process is carried out under two constraints: the normalization of the weighted point spread function for the principal isotope (X) is required to match that of the point spread function using a standard fixed energy window, and the values for the different terms of the weighting function are maintained within the limits required by the imaging hardware.

The ideal weighting function is required to adhere to the constraint that where a weighting function is used, e.g. for two isotopes X and Y, the weighting function for isotope X in the presence of isotope Y produce a good point spread function for X and a zero or non-peaked point spread function for isotope Y, and likewise for the weighting function for isotope Y in the presence of X.

Although a preferred embodiment has been described above, the scope of the invention is limited only by the following claims:

I claim:

1. A method of conducting a multi-isotope study using a gamma camera and a plurality of isotopes, comprising the step of weighting information acquired by the gamma camera with as many weighting functions as there are isotopes.

2. The method of claim 1, further comprising the step of producing as many planar images as there are isotopes.

3. The method of claim 1, further comprising the step of producing as many tomographic images as there are isotopes.

4. A method of conducting a multi-isotope study using a gamma camera and a plurality of isotopes, said gamma camera producing information in an event-by-event format, the method comprising the step of weighting the information in real time using as many energy-based weighting functions as there are isotopes and producing as many images as there are isotopes.

5. A method of conducting a multi-isotope study using a gamma camera and a plurality of isotopes, said gamma camera producing information, in an event-by-event format, the method comprising the step of weighting the information using as many energy-based weighting functions as there are isotopes and producing as many images as there are isotopes, said weighting step being carried out in a post-processing mode after all the information has been accumulated.

6. A method of conducting a multi-isotope study using a gamma camera and a plurality of isotopes. said gamma camera producing information in a frame-by-frame format, the method comprising the step of weighting the information using as many energy-based weighting convolution functions as there are isotopes and producing as many images as there are isotopes, said weighting step being carried out in a post-processing mode after all the information has been accumulated.

7. A method of conducting a multi-isotope study using a gamma camera and a plurality of isotopes, said gamma camera producing information in a region-by-region format, the method comprising the step of spectrally deconvolving the information using as many energy spectrum-based deconvolution functions as there are isotopes and producing as many images as there are isotopes, said deconvolving step being carried out in a post-processing mode after all the information has been accumulated.

* * * * *